(12) United States Patent
Graham

(10) Patent No.: US 6,955,432 B2
(45) Date of Patent: Oct. 18, 2005

(54) CONTACT LENS PLACEMENT INSTRUMENT

(76) Inventor: Neil John Graham, 6017 Lido La., Long Beach, CA (US) 90803

( * ) Notice: Subject to any disclaimer, the term of this patent is extended or adjusted under 35 U.S.C. 154(b) by 226 days.

(21) Appl. No.: 10/405,364

(22) Filed: Apr. 3, 2003

(65) Prior Publication Data

US 2004/0196430 A1 Oct. 7, 2004

(51) Int. Cl.⁷ .............................. G02C 7/04; A61F 9/00
(52) U.S. Cl. ..................... 351/160 H; 294/1.2; 351/177
(58) Field of Search ....................... 351/160 R, 160 H, 351/177; 294/1.2; 359/802–805

(56) References Cited

U.S. PATENT DOCUMENTS

| 4,123,098 A | * | 10/1978 | Shoup | 294/1.2 |
| 5,050,918 A | * | 9/1991 | Kolze | 294/1.2 |
| 6,441,969 B1 | * | 8/2002 | Goldstein et al. | 359/727 |

* cited by examiner

Primary Examiner—Scott J. Sugarman
(74) Attorney, Agent, or Firm—Neil John Graham

(57) ABSTRACT

A contact lens placement instrument which places a contact lens on the eye and, using a puff of air releases the lens, the procedure may be performed with a corrective lens or a magnifying mirror which contain lighting illuminating the eye.

20 Claims, 4 Drawing Sheets

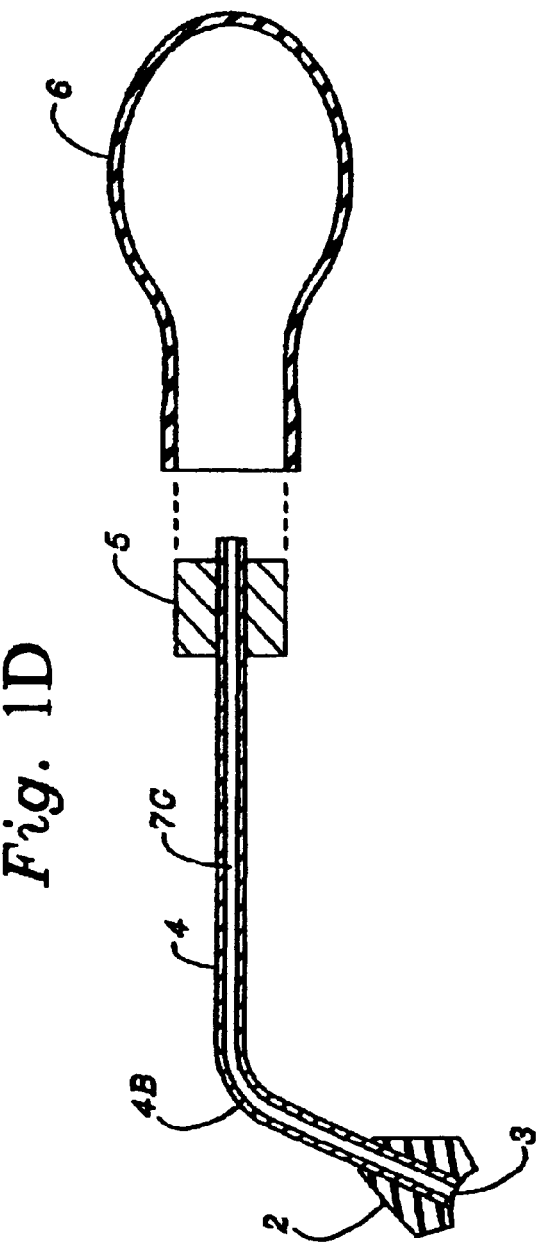
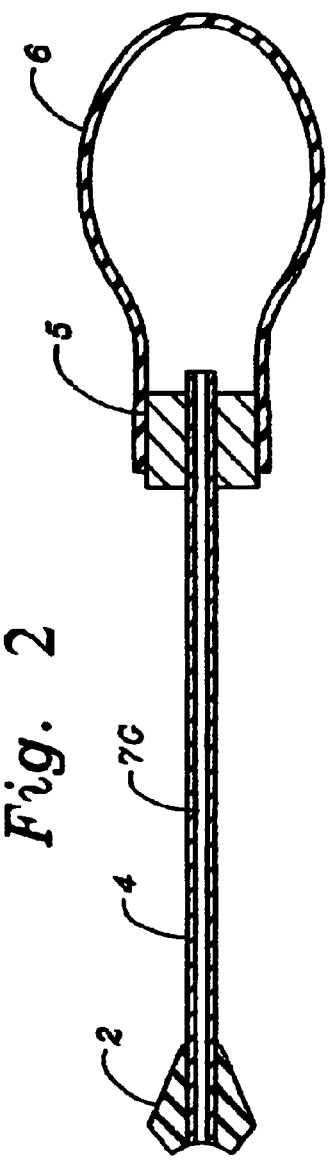

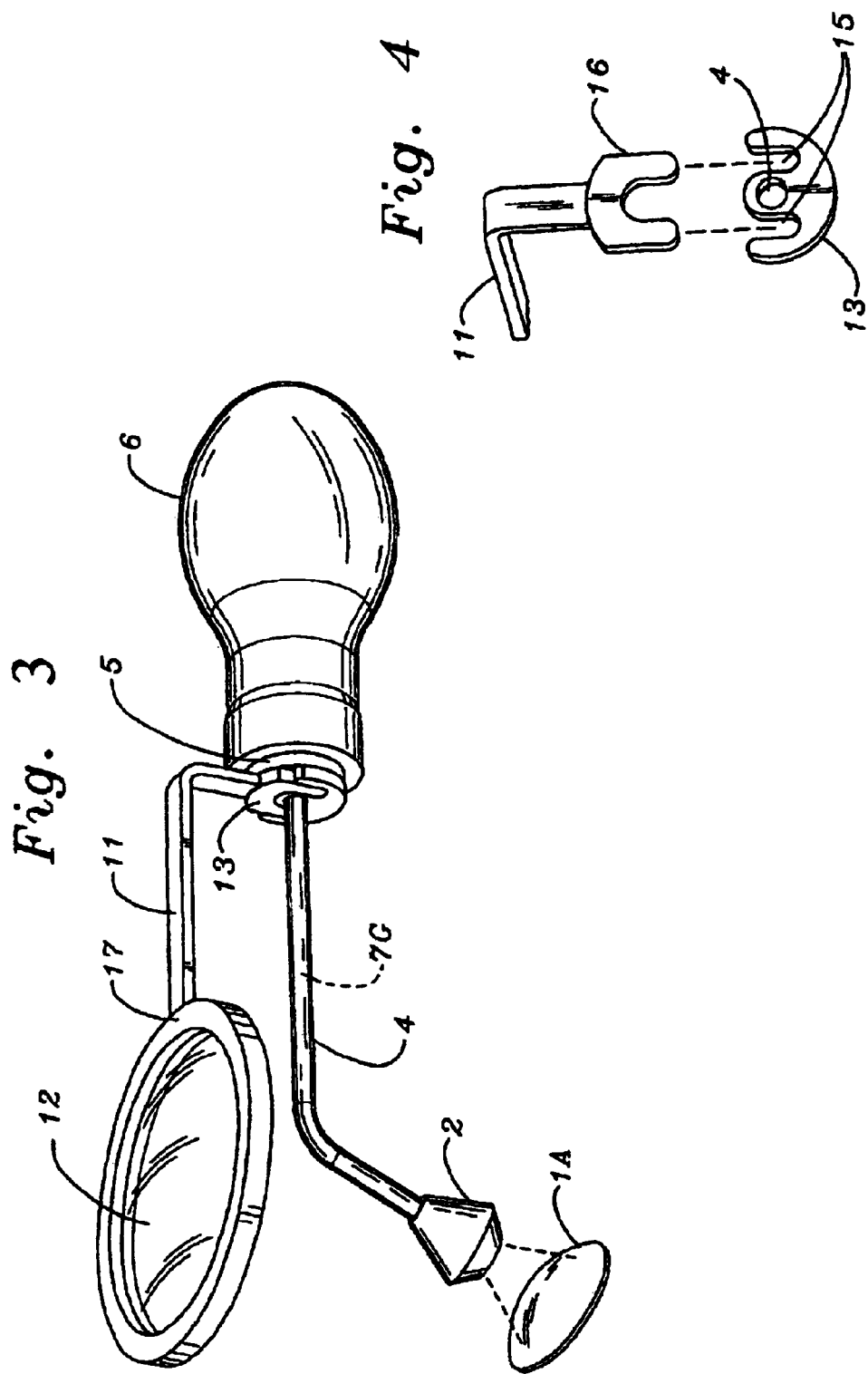

CONTACT LENS PLACEMENT INSTRUMENT

FIELD OF INVENTION

The present invention is directed to an instrument for placing a contact lens on an eye, most effective in the release of the contact lens once it has been seated on the eyeball.

BACKGROUND OF THE INVENTION

Contact lenses are most commonly placed on the eye by first placing the outer curvature of a contact lens on a finger tip. The contact lens is then directed towards and seated against the eyeball where a liquid seal is formed between the eyeball and lens. The finger is removed from the lens and the lens remains seated on the eye. The contact lens frequently won't release and remains on the finger, requiring another attempt at installation of the contact lens. Placement of contact lens using fingers brings in the question of how sanitary the fingers are.

SUMMARY OF THE INVENTION

The present intention is directed towards an instrument which is used to carry a contact lens to a person's eye and releasing the lens from the instrument with a puff of air once the lens has been seated on the eyeball. The invention is applicable to placing a hard contact lens, but is most effective for placement of a soft contact lens.

The contact lens placement instrument is comprised of a cylindrical tube approximately 80–100 mm in length. The outside diameter of the tube is 1–1.5 mm depending upon the material used. The interior is hollow and 1 mm in diameter. The material may be plastic or metal, such as stainless steel. One end of the tube contains a contact lens holder comprised of a tissue compatible material, such a silicone, which has an end shaped to fit the outside curvature of the contact lens. The lens contacting portion is a cylindrical conical area with a diameter of 4–6 mm and has a central hole connected to the hollow tube. A softer silicone is desirable, but not necessarily. The last 20 mm of the other end of the tube enlarges into six mm in diameter is fitted to a hollow rubber air bulb, the center of the air bulb connecting to the hollow center of the tube.

The outer curvature of the contact lens is placed on the conical end of the lens holder and the lens is then carried to the eyeball and seated. Once the lens is seated the air bulb is squeezed as the instrument is removed from the eye. The puff of air effectively disengages the instrument from the contact lens and the lens is left fitted to the eye.

In another embodiment of the invention the last 20–30 mm of the tube on the lens holder end is 90° to the body of the tube. This bend allows the air bulb to be out of the line of vision which allows a clearer view of the eye. In another embodiment the lens holder is removable. There is a female cavity in the lens holder which receives the end of the hollow tube. The hollow tube is shaped to fit the female cavity. The interior of the female cavity is bulbous, or larger in diameter than its opening. The hollow tube end is shaped to match the female cavity. This provides a locking of the lens holder on the end of the hollow tube. The lens holder is removable which allows it to be replaced, as needed, or it can be disposable with every use. Disposable is desirable if the contact lens replacement tool is used on multiple patients.

In another embodiment the lens holder conical area is extended into a larger cone which is contoured to fit the outer curvature of the contact lens. This extension is porous foam, preferably made from silicone. The object of the extension is to aid in seating the lens to surface of the eye with a material which won't adhere to the contact lens during the removal process of the lens placement after lens placement.

Mounted to the bulb end of the hollow tube are female slots for receiving a removable eyeglass lens holder, the holder having appropriately sized male members to removably fit into the female slots. The other end of the eyeglass holder has a clip mechanism to hold the eyeglass lens. The lens is positioned relative to the eye similarly to a pair of glasses but of sufficient distance from the eye to allow for the contact placement instrument. In the embodiment with the curved hollow tube the eyeglass lens would be in the axial direction of the lens holder portion of the hollow tube. The lens would be 20–30 mm from the bend area of the hollow tube. When a person uses the contact lens installing instrument to install the lens they can, by using a mirror, focus upon their eye during lens installation which greatly facilitates the contact lens placement. This is especially useful for people who have poor near vision.

Another embodiment of invention is a magnifying mirror, the same size as the eyeglass lens, placed in the same position as the lens. The mirror allows a person to install contact lenses when mirrors are not available. This use of a mirror allows a person to have a hand free to pull the lower eyelid down during the contact lens installation. The mirror would have the necessary corrective magnification for the person using it. In another embodiment of the corrective lens and the mirror a light means is attached with a power source for illumination of the eye during the installation of the contact lens. Using the magnifying mirror the contact lens could be placed in the dark.

In another embodiment the hollow tube is constructed from the plastic containing a 10 gauge solid copper wire within its hollow center which allows the tube to be bent and having enough rigidity to hold the new shape.

The use of the contact lens placement instrument is as follows. The outer curvature of the contact lenses is placed on the lens holder and carried to the eye where it is seated. Once the lens is seated the air bulb is squeezed producing a puff of air to the lens which releases the contact lens from the contact lens placement instrument. As this is done the contact lens placement instrument is pulled away from the eye. The puff of air effectively releases the contact lens. The contact lens placement instrument also has the advantage of providing a method of placing a contact lens without placing a finger in the eye, making the process more sanitary.

BRIEF DESCRIPTION OF THE DRAWINGS

FIG. 2 is another embodiment of the present invention;

FIG. 3 is another embodiment of the present invention;

FIG. 4 is a view of the removable attachment;

DETAILED DESCRIPTION OF THE INVENTION

Figure 1A:
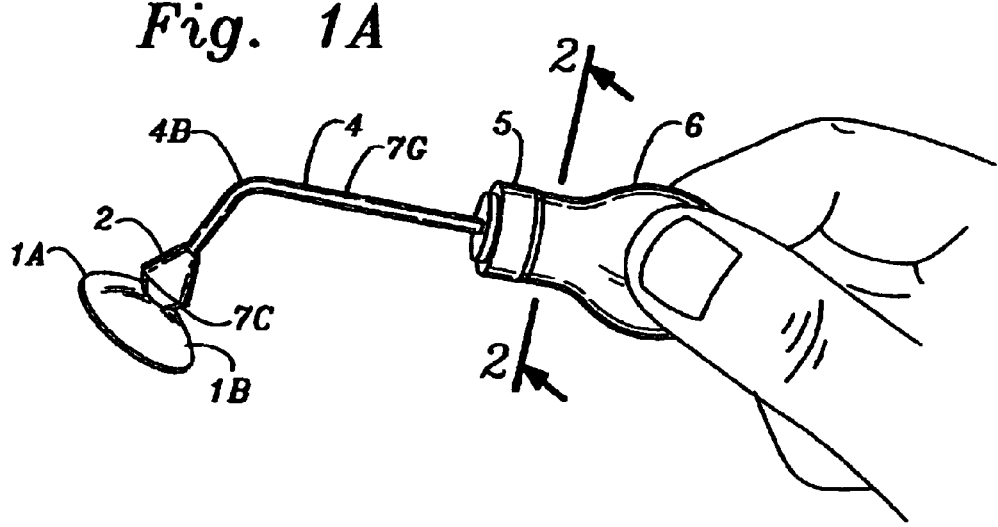
FIG. 1 is a view of the contact lens placement instrument with selected views of the lens holder.
Figure 1B:
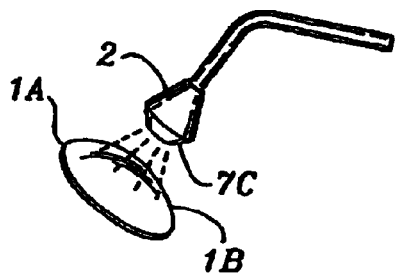
Figure 1C:
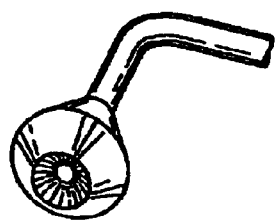

Referring to FIGS. 1, 2, 3, and 4 the contact lens placement instrument is comprised of a lens holder 2 and 32. The lens holder 2 and 32 is comprised of a tissue compatible silicone. The lens holder 2 and 32 has a conical surface 7A which is curved from lip to lip 7B to match the outer curvature 1B of a contact lens 1A. The conical surface 7 is 2–4 mm in diameter. The side walls 7C of the lens holder 2 taper from the conical lip 7B away from the conical surface 7A and converge to enclose a hollow tube 4 as shown in FIGS. 1, 2 and 3. A preferred embodiment of the side wall 7C curvature is shown in FIG. 1 wherein the side wall 7C flares out from the conical lip 7B, like a skirt, then changes direction 7D and tapers in. This makes the conical lip 7B less acute making the lip 7B less likely to injure the eyeball. There is a hollow longitudinal channel running in the center of the lens holder 2 running in a longitudinal axial direction communicating from the surface 7A of the lens holder 2 to the opposite end.

A hollow tube 4 approximately 2 mm in diameter with a 1 mm hollow interior 7G is connected to the lens holder 2. The hollow tube 4 is in the same axial direction as the lens holder 2 at its point of attachment. The hollow interior 7G of the tube 4 connects with the hollow longitudinal channel 7F of the lens holder 2. In one embodiment as shown in FIG. 2 the hollow tube 4 extends in a straight axial direction approximately 80 mm where it enlarges into a hollow fitting 5 with an outer diameter of 6 mm and a length of 20 mm. In FIGS. 1, 2, and 3 a 30 mm air bulb 6A, with a 6 mm diameter open end 6B, is fitted over the fitting 5. The contact lens placement instrument is used to insert a contact lens 1A on the surface of the eyeball and then effectively releases the contact lens 1A when it is in place. The contact lens placement instrument is grasped with one hand by the air bulb 6A. The wet contact lens 1A is mounted by its outside curvature surface 1B to the conical surface 7A of the lens holder 2. A finger from the opposite hand pulls the lower eyelid downwards and the contact lens 1A is inserted on the front of the eyeball. Once a contact lens 1A is securely seated the contact lens placement instrument is removed from the eye as the air bulb 6A is squeezed. A puff of air travels through the hollow tube 4 and hollow lens holder 2 and exits the hole 7F in the conical cup 7A and hits the outer surface 1B of the contact lens 1A and releases the contact lens 1A.

Figure 5:
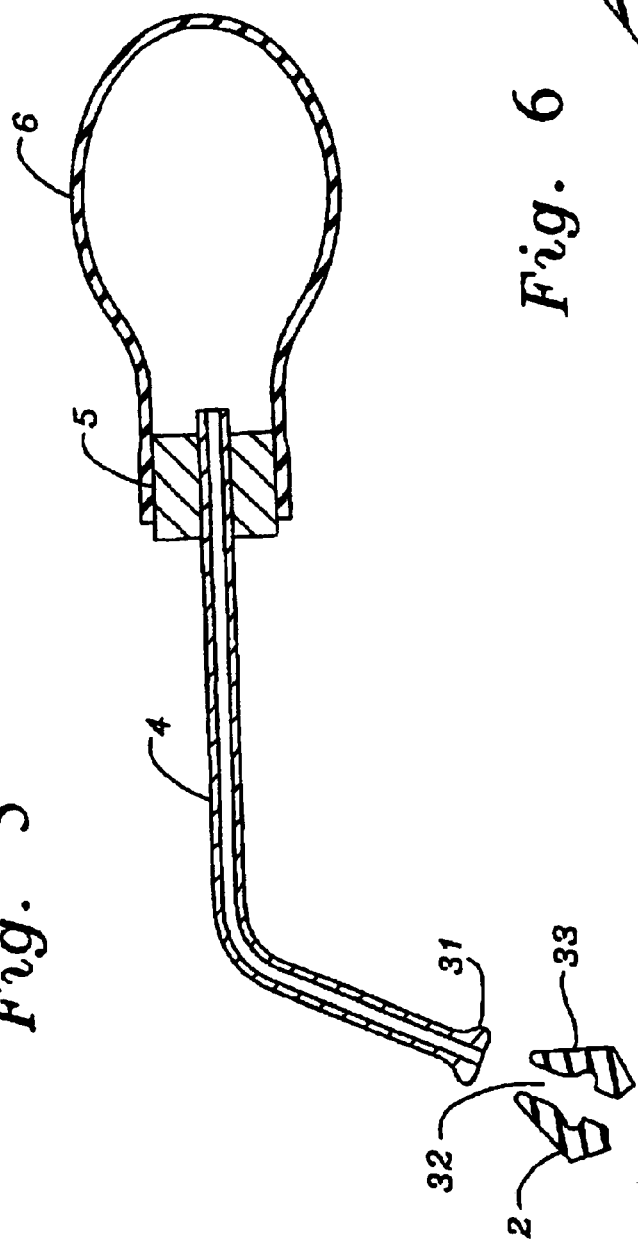
FIG. 5 is another embodiment of the invention.

In FIGS. 1, 3 and 5 another preferred embodiment is shown where the hollow tube 4 has a 90° bend 4B in it. The hollow tube 4 extends approximately 20–30 mm from the lens holder 2 and makes the right angle bend 4B wherein the hollow tube 4 extends 60 mm where it ends in the fitting 5 for the air bulb 6A. The hollow tube 4 can be made from plastic or metal, such as stainless steel. The hollow tube 4 can be a combination of materials.

In FIG. 5A a preferred embodiment of the lens holder is removable which allows its removal for sterilization or replacement, especially if the lens holder is disposable. The lens holder 2 has an interior bulbous female cavity which faces the hollow tube 4. The end of the hollow tube is flared 31 or bulbous and sized to fit into the female fitting 32 of the lens holder 2. Referring to FIGS. 3 and 4 another preferred embodiment has a corrective eyeglass sized lens 12, or magnifying mirror 12, is mounted to the contact lens positioning instrument allowing the eye to be clearly viewed during the installation of the contact lens 1A. The angled hollow tube 4 is desirable because the corrective lens 12 or mirror 12 can be placed 10–20 mm from the hollow tube 4 and in the axial direction of the lens holder 2 portion of the hollow tube 4. The horizontal plane of the magnifying lens 12 is at a right angle to the longitudinal axis of lens holder 2 portion of the hollow tube 41. With the lens positioned in this area during the installation of the contact lens 1A the eye can be clearly viewed. A magnifying mirror 12 can be mounted in the same position eliminating the need for a hand held or wall mounted mirror.

A preferred embodiment for mounting the mirror 12 or lens 12 is shown in FIGS. 3 and 4. A lens holder 11 is used with a gripping means 17 at one end for attaching the mirror 12 or lens 12. The other end of the lens holder 11 has removable mount 13. The removal mount 13 is comprised of a female part 15 and is mounted to the tube end of the fitting 5. In FIG. 4 the female receptacle 15, mounted to the hollow tube 4 side of the fitting 5, removably receives matching male receptacles 16 which are connected to the end of the lens holder 11. The lens holder 11 extends 20 mm away from the hollow tube 4 then turns and follows the direction of the hollow tube 4 where it ends with a gripping means 17 to hold the lens 12 or mirror 12.

In another embodiment of the invention the magnifying mirror 12 or lens 12 contains a lighting means for illuminating the eye. The lighting means is particularly useful for placing the contact lens 1A in poor lighting or in the dark. The lighting means is comprised of a low energy consuming LED light which would only require a miniature battery, such as a watch battery.

Figure 6:
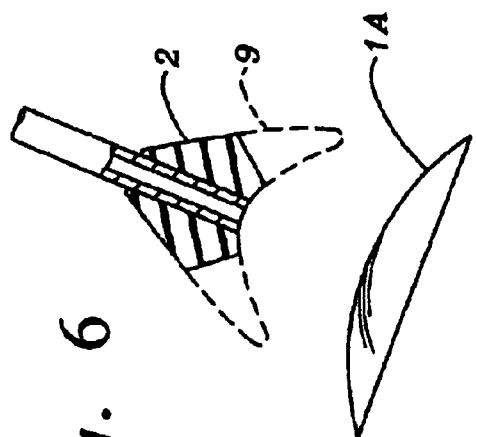
FIG. 6 is another embodiment of the lens holder.

Another embodiment of the contact lens placement instrument is shown in FIG. 6 wherein a porous foam extension 9 of the curved portion 7A of the lens holder 1A is extended following the same curvature as the contact lens to slightly less than the diameter of the contact lens 1A, ideally a biocompatible material, such as silicone. The foam portion 9 is helpful in seating the contact lens 1A on the eyeball.

The invention has been described in several embodiments, but is intended to include variations of what has been described. The invention uses a gas, such as air, to place and release a contact lens. The invention eliminates the use of fingers in the eye during the placement of the contact lens.

What is claimed:

1. A contact lens placement instrument for placing and releasing a contact lens comprising:
    an axial longitudinal hollow tube with a first end, second end, and an exterior and an interior wherein the interior is hollow and 1 mm in diameter from the first end to the second end;
    a contact lens holder with an axial direction, a first end and a second end, an interior and exterior sides, the interior is hollow and 1 mm in diameter from the first end to the second end wherein the first end receives the first end of the longitudinal hollow tube and the second holder end has a recessed conical surface 4–6 mm in diameter shaped to receive the outside curvature of the surface of a contact lens; and
    an air bulb with a hollow interior connected to the second end of the hollow tube wherein a contact lens is placed on the conical surface of the contact lens holder with the inside of the lens curvature facing towards the eye, the lens is carried to and seated on the eye, the air bulb is squeezed which delivers a puff of air to the contact lens surface as the contact lens placement instrument is removed from the eye, the puff of air effectively releasing the contact lens from the lens holder.

2. A contact lens placement instrument as in claim 1 wherein the exterior diameter is 2–3 mm and the axial longitudinal length is 80 mm.

3. A contact lens placement instrument as in claim 1 wherein the lens holder sides start at the second lens holder end and travel towards the first lens holder end at 45° to the lens holder longitudinal axis, at 3–4 mm the sides gently curve inward towards the center of the lens tube long axis, the object is to make the side conical surface angle less acute to prevent injury to the eye.

4. A contact lens placement instrument as in claim 1 wherein the placement instrument is 6–8 mm in length and comprised of silicone.

5. A contact lens placement instrument as in claim 1 wherein the axial longitudinal hollow tube is comprised of a plastic material or metal, such as stainless steel.

6. A contact lens placement instrument as in claim 1 wherein a hollow cylindrical fitting is attached to the second end of the hollow tube, the cylindrical fitting is 12 mm in length and 6 mm in diameter and the air bulb is attached with the internal air chamber connecting to the interior of the hollow tube.

7. A contact lens placement instrument comprising:
an axial longitudinal hollow tube with a first end, second end, and an exterior and an interior wherein the interior is hollow and 1 mm in diameter from the first end to the second end, the hollow tube has a right angle bend between its first and second one-third, nearest its first end;
a contact lens holder with an axial direction, a first end and a second end, an interior and exterior sides, the interior is hollow and 1 mm in diameter from the first end to the second end wherein the first end receives the first end of the longitudinal hollow tube and the second holder end has a recessed conical surface 4–6 mm in diameter shaped to receive the outside curvature of the surface of a contact lens; and
an air bulb with a hollow interior connected to the second end of the hollow tube wherein a contact lens is placed on the conical surface of the contact lens holder with the inside of the lens curvature facing towards the eye, the lens is carried to and seated on the eye, the air bulb is squeezed which delivers a puff of air to the contact lens surface as the contact lens placement instrument is removed from the eye, the puff of air effectively releasing the contact lens from the lens holder.

8. A contact lens placement instrument as in claim 7 wherein the hollow tube exterior diameter is 2–3 mm and the axial longitudinal length is 80 mm.

9. A contact lens placement instrument as in claim 7 wherein the lens holder sides start at the second lens holder end and travel towards the first lens holder end at 45° to the lens holder longitudinal axis, at 3–4 mm the sides gently curve inward towards the center of the lens tube long axis, the object is to make the side conical surface angle less acute to prevent injury to the eye.

10. A contact lens placement instrument as in claim 7 wherein the placement instrument is 6–8 mm in length and comprised of silicone.

11. A contact lens placement instrument as in claim 7 wherein the axial longitudinal hollow tube is comprised of a plastic material or metal, such as stainless steel.

12. A contact lens placement instrument as in claim 7 wherein a hollow cylindrical fitting is attached to the second end of the hollow tube, the cylindrical fitting is 12 mm in length and 6 mm in diameter and the air bulb is attached with the internal air chamber connecting to the interior of the hollow tube.

13. A contact lens placement, instrument comprising:
an axial longitudinal hollow tube with a first end, second end, and an exterior and an interior wherein the interior is hollow and 1 mm in diameter from the first end to the second end, the hollow tube has right angle bend between its first and second one-third nearest its first end;
a contact lens holder with an axial direction, a first end and a second end, an interior 1 mm in diameter and exterior sides, the interior is hollow from the first end to the second end wherein the first end receives the first end of the longitudinal hollow tube and the second holder end has a recessed conical surface 4–6 mm in diameter shaped to receive the outside curvature of the surface of a contact lens;
an air bulb with a hollow interior connected to the second end of the hollow tube wherein a contact lens is placed on the conical surface of the contact lens holder with the inside of the lens curvature facing towards the eye, the lens is carried to and seated on the eye, the air bulb is squeezed which delivers a puff of air to the contact lens surface as the contact lens placement instrument is removed from the eye, the puff of air effectively releasing the contact lens from the lens holder;
a corrective lens and holder removably mounted to the lens placement instrument wherein the lens is corrective for the user and allows a clear view of the eye enabling installation or removal of the contact lens; and
a corrective mirror and holder removably mounted to the lens placement instrument wherein the mirror is corrective for the user and allows a clear view of the eye enabling installation or removal of the contact lens.

14. A contact lens placement instrument as in claim 13 wherein the hollow tube exterior diameter is 2–3 mm and the axial longitudinal length is 80 mm.

15. A contact lens placement instrument as in claim 13 wherein the lens holder sides start at the second lens holder end and travel towards the first lens holder end at 45° to the lens holder longitudinal axis, at 3–4 mm the sides gently curve inward towards the center of the lens tube long axis, the object is to make the side conical surface angle less acute to prevent injury to the eye.

16. A contact lens placement instrument as in claim 13 wherein the placement instrument is 6–8 mm in length and comprised of silicone.

17. A contact lens placement instrument as in claim 13 wherein the axial longitudinal hollow tube is comprised of a plastic material or metal, such as stainless steel.

18. A contact lens placement instrument as in claim 13 wherein a hollow cylindrical fitting is attached to the second end of the hollow tube, the cylindrical fitting is 12 mm in length and 6 mm in diameter and the air bulb is attached with the internal air chamber connecting to the interior of the hollow tube.

19. A contact lens placement instrument as in claim 13 wherein the corrective lens and corrective mirror are illuminated by a lighting means which provides light to the eye area.

20. A contact lens placement instrument as in claim 13 wherein the lighting means is LED light bulbs which require little energy, the energy source can be as small as a watch battery.

* * * * *